United States Patent [19]
Kobayashi et al.

[11] 3,966,939
[45] June 29, 1976

[54] NOVEL 2-SUBSTITUTED 6,7-BENZOMORPHAN DERIVATIVES AND SALTS THEREOF IN ANALGESIC COMPOSITIONS

[75] Inventors: Kenji Kobayashi, Takarazuka; Toshitsugu Fukumaru, Kyoto; Hiroyuki Mizote; Shigeho Inaba, both of Takarazuka; Hisao Yamamoto, Nishinomiya, all of Japan

[73] Assignee: Sumitomo Chemical Company, Limited, Japan

[22] Filed: Mar. 17, 1975

[21] Appl. No.: 558,655

Related U.S. Application Data

[62] Division of Ser. No. 418,052, Nov. 21, 1973, Pat. No. 3,903,093.

[30] Foreign Application Priority Data
Nov. 22, 1972 Japan.............................. 47-117379

[52] U.S. Cl. ................................................ 424/260
[51] Int. Cl.² ........................................ A61K 31/485
[58] Field of Search .................................... 424/260

[56] References Cited
UNITED STATES PATENTS
3,632,591  1/1972  Albertson et al. ........... 260/DIG. 13
3,776,914  12/1973  Atsumi et al. ............... 260/DIG. 13

Primary Examiner—Stanley J. Friedman
Attorney, Agent, or Firm—Craig & Antonelli

[57] ABSTRACT

Novel 2-substituted 6,7-benzomorphan derivatives of the formula:

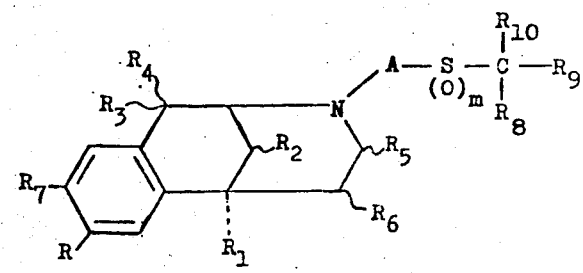

and acid addition salts thereof, which are useful as non-addicting analgesics, pain relieving agents and antitussives and can be prepared by reacting 6,7-benzomorphan derivatives of the formula:

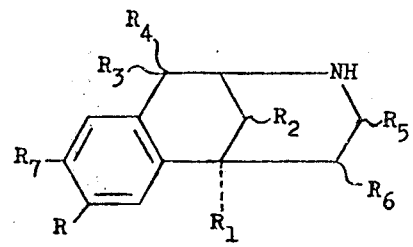

with the reactive derivatives of alcohols of the formula:

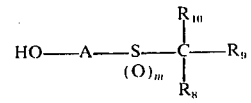

[wherein R is a hydrogen atom, a hydroxyl group, an alkoxy group or an alkanoyloxy group; $R_1$ is a hydrogen atom, an alkyl group, an alkoxyalkyl group or a substituted or unsubstituted aryl group; $R_3$ is a hydrogen atom or a hydroxyl group; $R_4$ is a hydrogen atom, an alkyl group or a substituted or unsubstituted aryl group, or $R_3$ and $R_4$ may form an alkylidene group or a carbonyl group together with the carbon atom to which these substituents are bonded; $R_2$, $R_5$, $R_6$, $R_7$, $R_8$, $R_9$ and $R_{10}$ are each a hydrogen atom or an alkyl group; A is an alkylene group; and m is an integer of 0 to 2].

15 Claims, No Drawings

NOVEL 2-SUBSTITUTED 6,7-BENZOMORPHAN DERIVATIVES AND SALTS THEREOF IN ANALGESIC COMPOSITIONS

CROSS-REFERENCE TO RELATED APPLICATION

This is a division of application Ser. No. 418,052 filed Nov. 21, 1973 and now U.S. Pat. No. 3,903,093.

The present invention relates to novel 2-substituted benzomorphan derivatives and their acid addition salts, which are useful as non-addicting analgesics, pain-relieving agents and antitussives, and their production and compositions containing them.

Hitherto, many benzomorphan derivatives (e.g., phenazocine, pentazocine) have been developed as analgesic drugs but most of them have addiction and produce narcotic symptoms at their usual dosages. The products of the invention do not show any drug dependency in animal tests.

Accordingly, a main object of the present invention is to provide benzomorphan derivatives which are useful as analgesic, pain-relieving and antitussive agents without addiction.

The present invention provides a novel 2-substituted 6,7-benzomorphan derivative of the formula:

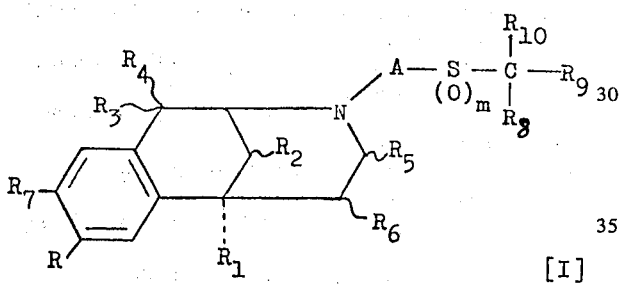

[wherein R is a hydrogen atom, a hydroxyl group, a $C_1$–$C_3$ alkoxy group or a $C_1$–$C_8$ alkanoyloxy group; $R_1$ is a hydrogen atom, a $C_1$–$C_5$ alkyl group, a $C_2$–$C_{10}$ alkoxyalkyl group, a phenyl group, a halophenyl group, an alkylphenyl group (wherein the alkyl moiety has 1 to 3 carbon atoms) or an alkoxyphenyl group (wherein the alkoxy moiety has 1 to 3 carbon atoms); $R_3$ is a hydrogen atom or a hydroxyl group; $R_4$ is a hydrogen atom, a $C_1$–$C_3$ alkyl group, a phenyl group, a halophenyl group, an alkylphenyl group (wherein the alkyl moiety has 1 to 3 carbon atoms) or an alkoxyphenyl group (wherein the alkoxy moiety has 1 to 3 carbon atoms), or $R_3$ and $R_4$ may form a $C_1$–$C_3$ alkylidene group or a carbonyl group together with the carbon atom to which they are bonded; $R_2$, $R_5$, $R_6$, $R_7$, $R_8$, $R_9$ and $R_{10}$ are each a hydrogen atom or a $C_1$–$C_3$ alkyl group; A is a $C_1$–$C_3$ alkylene group; and $m$ is an integer of 0 to 2], and its non-toxic pharmaceutically acceptable acid addition salts.

A preferred class of compounds are the 2-substituted 6,7-benzomorphan derivatives of the formula [I] wherein R is a hydrogen atom, a hydroxyl group, a $C_1$–$C_3$ alkoxy group or a $C_1$–$C_8$ alkanoyloxy group, $R_1$ is a hydrogen atom, a $C_1$–$C_5$ alkyl group or a phenyl group, $R_3$, $R_4$, $R_5$ and $R_7$ are each a hydrogen atom, $R_2$, $R_6$, $R_8$, $R_9$ and $R_{10}$ are each a hydrogen atom or a $C_1$–$C_3$ alkyl group and $m$ is an integer of 0 to 2, and their acid addition salts.

A particularly preferred class of compounds are the 2-substituted 6,7-benzomorphan derivatives of the formula [I] wherein R is a hydroxyl group, $R_1$ is a hydrogen atom, a $C_1$–$C_3$ alkyl group or a phenyl group, $R_3$, $R_4$, $R_5$ and $R_7$ are each a hydrogen atom, $R_2$ and $R_6$ are each a hydrogen atom or a $C_1$–$C_3$ alkyl group, $R_8$, $R_9$ and $R_{10}$ are each a hydrogen atom or a methyl group and $m$ is an integer of 0, and their acid addition salts.

This invention further provides a process for producing the 2-substituted 6,7-benzomorphan derivative [I], which comprises reacting a 6,7-benzomorphan derivative of the formula:

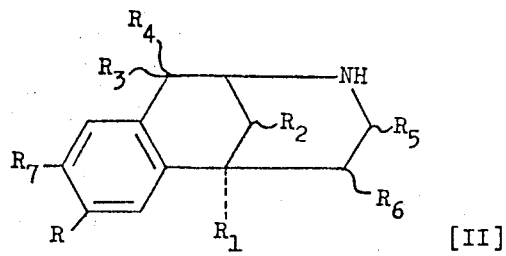

wherein R, $R_1$, $R_2$, $R_3$, $R_4$, $R_5$, $R_6$ and $R_7$ are each as defined above with a reactive derivative of an alcohol of the formula:

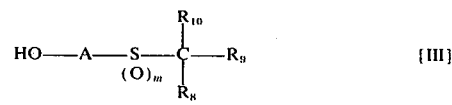

wherein $R_8$, $R_9$, $R_{10}$, A and $m$ are each as defined above. The reactive derivative of an alcohol stated above involves derivatives of an alcohol of which the hydroxyl group is replaced by an arylsulfonyloxy group (e.g. tosyloxy), an alkylsulfonyloxy group (e.g. methylsulfonyloxy) or a halogen atom.

The invention furthermore provides a novel pharmaceutical composition containing an analgesically effective amount of the 2-substituted 6,7-benzomorphan derivative [I] as an active ingredient and a pharmaceutically acceptable carrier or diluent.

The starting 6,7-benzomorphan derivative [II] is known and can be prepared by demethylating the corresponding 2-methyl-6,7-benzomorphan derivative. Thus, for example, U.S. Pat. No. 3,138,603 discloses a process shown by the following scheme:

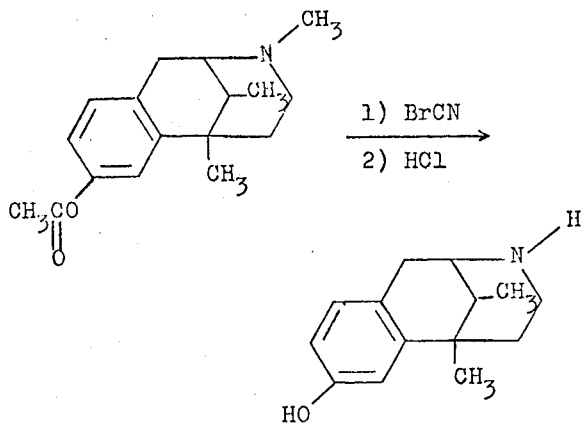

The reaction of the 6,7-benzomorphan derivative [II] with the reactive derivative of an alcohol [III] is usually carried out in an inert solvent (e.g. n-hexane, benzene, toluene, xylene, chloroform, dimethylformamide, methanol, ethanol, isopropanol). The presence of a basic substance (e.g. sodium carbonate, potassium carbonate, sodium bicarbonate, potassium bicarbonate, sodium hydroxide, potassium hydroxide, sodium amide, sodium hydride, pyridine, triethylamine) in the reaction is preferred. The reaction proceeds at a temperature of 20° to 200°C, preferably 50° to 150°C. The reaction product is readily recovered from the reaction mixture by a conventional separation procedure such as filtration or precipitation.

For the production of the 2-substituted 6,7-benzomorphan derivative [I : R = alkanoyloxy], the corresponding 2-substituted 6,7-benzomorphan derivative [I : R = hydroxyl] may be acylated by a per se conventional procedure, e.g. treating with an acid anhydride or an acyl halide.

When $R_2$ is alkyl, the 2-substituted 6,7-benzomorphan derivative [I] has two stereo isomers, i.e. cis isomer ($R_2$ being α-configuration) and trans isomer ($R_2$ being β-configuration). Each of these isomers can be separated and purified by a per se conventional procedure such as fractional crystallization, fractional distillation or column chromatography. Alternatively, each of these isomers may be produced from the corresponding cis or trans isomer of the 6,7-benzomorphan derivative [II] by reacting the same with the reactive derivative of an alcohol [III]. Still, each of the said isomers has asymmetric carbon atoms, and there can be obtained four optically active isomers (i.e. (+)-cis, (−)-cis, (+)-trans, (−)-trans) by a conventional optical resolution procedure.

The 2-substituted 6,7-benzomorphan derivative [I] possesses a basic nitrogen atom in the fundamental structure and hence various acid addition salts can be obtained by the use of organic and inorganic acids such as formic acid, acetic acid, propionic acid, butyric acid, malic acid, fumaric acid, succinic acid, glutamic acid, tartaric acid, oxalic acid, citric acid, lactic acid, maleic acid, hydroxymaleic acid, glycolic acid, gluconic acid, glucuronic acid, saccharic acid, ascorbic acid, phenylacetic acid, benzoic acid, p-aminobenzoic acid, phthalic acid, salicylic acid, anthranilic acid, p-hydroxybenzoic acid, p-aminosalicylic acid, picolinic acid, 3-hydroxy-2-naphthoic acid, 3-indoleacetic acid, barbituric acid, sulfamic acid, quininic acid, tropic acid, methanesulfonic acid, ethanesulfonic acid, benzenesulfonic acid, p-toluenesulfonic acid, hydroxyethanesulfonic acid, hydrofluoric acid, hydrochloric acid, hydrobromic acid, hydroiodic acid, perchloric acid, nitric acid, sulfuric acid, phosphoric acid and the like.

According to the present invention, the following 2-substituted 6,7-benzomorphan derivatives [I], and acid addition salts thereof can be obtained:

2-(β-Methylthioethyl)-6,7-benzomorphan;
2'-Hydroxy-2-(β-methylthioethyl)-6,7-benzomorphan;
2'-Methoxy-2-(β-methylthioethyl)-6,7-benzomorphan;
2'-Acetoxy-2-(β-methylthioethyl)-6,7-benzomorphan;
2'-Hydroxy-2-(β-isopropylthioethyl)-6,7-benzomorphan;
2-(β-Methylthioethyl)-5-methyl-6,7-benzomorphan;
2'-Hydroxy-2-(β-methylthioethyl)-5-methyl-6,7-benzomorphan;
2'-Methoxy-2-(β-methylthioethyl)-5-methyl-6,7-benzomorphan;
2'-Acetoxy-2-(β-methylthioethyl)-5-methyl-6,7-benzomorphan;
2'-Hydroxy-2-(β-isopropylthioethyl)-5-methyl-6,7-benzomorphan;
2-(β-Methylthioethyl)-5-ethyl-6,7-benzomorphan;
2'-Hydroxy-2-(β-methylthioethyl)-5-ethyl-6,7-benzomorphan;
2'-Methoxy-2-(β-methylthioethyl)-5-ethyl-6,7-benzomorphan;
2'-Acetoxy-2-(β-methylthioethyl)-5-ethyl-6,7-benzomorphan;
2'-Hydroxy-2(β-isopropylthioethyl)-5-ethyl-6,7-benzomorphan;
2'-Hydroxy-2-(β-methylsulfonylethyl)-5-ethyl-6,7-benzomorphan;
2'-Hydroxy-2-(β-methylthioethyl)-5,9-dimethyl-6,7-benzomorphan;
2'-Methoxy-2-(β-methylthioethyl)-5,9-dimethyl-6,7-benzomorphan;
2'-Acetoxy-2-(β-methylthioethyl)-5,9-dimethyl-6,7-benzomorphan;
2'-Hydroxy-2-(β-isopropylthioethyl)-5,9-dimethyl-6,7-benzormorphan;
2'-Hydroxy-2-(β-methylsulfinylethyl)-5,9-dimethyl-6,7-benzomorphan;
2'-Hydroxy-2-(β-methylsulfonylethyl)-5,9-dimethyl-6,7-benzomorphan;
2'-Hydroxy-2-(β-methylthioethyl)-5-ethyl-9-methyl-6,7-benzomorphan;
2'-Hydroxy-2-(β-methylthioethyl)-5-methyl-9-ethyl-6,7-benzomorphan;
2'-Hydroxy-2-(β-methylthioethyl)-5,9-diethyl-6,7-benzomorphan;
2'-Hydroxy-2-(β-methylthioethyl)-5-phenyl-6,7-benzomorphan;
2'-Hydroxy-3'-methyl-2-(β-methylthioethyl)-5,9-dimethyl-6,7-benzomorphan;
2'-Hydroxy-2-(β-methylthioethyl)-5,8,9-trimethyl-6,7-benzomorphan;
2'-Hydroxy-2-(β-methylthioethyl)-3,5,9-trimethyl-6,7-benzomorphan;
2'-Hydroxy-2-(β-methylthioethyl)-4,5,9-trimethyl-6,7-benzomorphan;
2'-Hydroxy-2-(β-methylthioethyl)-4,5-dimethyl-6,7-benzomorphan, etc.

6,7-Benzomorphan derivatives such as 2'-hydroxy-2,5,9-trimethyl-6,7-benzomorphan (U.S. Pat. No. 3,138,603) have a potent analgesic activity but show an addition liability. On account of this addiction liability, these analgesics are severely restricted in a therapeutic use. Surprisingly, the 2-substituted 6,7-benzomorphan derivatives [I] (e.g. 2'-hydroxy-2-(β-methylthioethyl)-5,9-dimethyl-6,7-benzomorphan, 2'-hydroxy-2-(β-methylthioethyl)-5,9-diethyl6,7benzomorphan, 2'-hydroxy-2-(β-methylthioethyl)-5-ethyl-6,7-benzomorphan) do not show addiction in long term animal tests. When, for example, these compounds were administered orally or subcutaneously to rats everyday for over one month, the animals did not produce any physical dependency as shown in Table 1.

Table 1

| Compound | Dose (mg/kg/day for 4 weeks) | Abstinence syndrome |
|---|---|---|
| 2'-Hydroxy-2-(β-methylthioethyl)-5,9-dimethyl-6,7-benzomorphan | 40 | — |
| 2'-Hydroxy-2-(β-methylthioethyl)-5,9-diethyl-6,7-benzomorphan | 40 | — |
| 2'-Hydroxy-2-(β-methylthioethyl)- | | |

Table 1-continued

| Compound | Dose (mg/kg/day for 4 weeks) | Abstinence syndrome |
| --- | --- | --- |
| 5-ethyl-6,7-benzomorphan | 20 | – |
| Morphine | 20 | +++ |
| 2'-Hydroxy-2,5,9-trimethyl-6,7-benzomorphan | 20 | ++ |

Note: Groups of male rats of Wistar strain (body weight, 150 g), each group consisting of 20 male rats, were subcutaneously given the test compound twice a day for 4 consecutive weeks. On the next day after drug withdrawal, the body weight was measured. The symbols have the following meanings: +++, severe decrease (about 5% decrease); ++, moderate decrease; +, mild decrease; –, no decrease. The marked decrease is taken as an indication of the possession of a narcotic property by the test compound.

Further, the 2-substituted 6,7-benzomorphan derivative [I] (e.g. 2'-hydroxy-2-($\beta$-methylthioethyl)-5,9-dimethyl-6,7-benzomorphan, 2'-hydroxy-2-($\beta$-methylthioethyl)-5-ethyl-6,7-benzomorphan, 2'-hydroxy-2-($\beta$-isopropylthioethyl)-5,9-dimethyl-6,7-benzomorphan) shows a strong analgesic activity. In a subcutaneous writhing test, for instance, they exhibited much more potent analgesic action than pentazocine (i.e. 2'-hydroxy-2-(3''-methyl-2''-butenyl)-5,9-dimethyl-6,7-benzomorphan), which is one of the strongest commercial analgesics, as shown in Table 2.

Table 2

| Compound | $ED_{50}$ (mg/kg) |
| --- | --- |
| 2'-Hydroxy-2-($\beta$-methylthioethyl)-5,9-dimethyl-6,7-benzomorphan | 3.1 |
| 2'-Hydroxy-2-($\beta$-methylthioethyl)-5-ethyl-6,7-benzomorphan | 0.34 |
| 2'-Hydroxy-2-($\beta$-isopropylthioethyl)-5,9-dimethyl-6,7-benzomorphan | 3.6 |
| Pentazocine (2'-hydroxy-2-(3''-methyl-2''-butenyl)-5,9-dimethyl-6,7-benzomorphan | 17.5 |

Note: The test was based on the specific anatagonism of the test compound to the typical syndrome produced by intraperitoneal injection of 0.6% aqueous acetic acid. The syndrome was characterized by intermittent contractions of the abdomen, twisting and turning of the trunk and extension of the hind legs. A group of 5 mice was used for each dose level. The test compound was administered subcutaneously 20 minutes before the injection of acetic acid. The number of mice which showed no pain response was recorded. The $ED_{50}$ value was calculated according to the Litchfeld-Wilcoxon's method.

The 2-substituted 6,7-benzomorphan derivatives [I] can be prepared for use by dissolving under sterile conditions a salt form of them in water (or an equivalent or more amount of a pharmaceutically acceptable acid if the free base is used instead of the salt), or in a physiologically compatible aqueous medium such as saline, and stored in ampoules for use by injection. Alternatively, they can be incorporated in unit dosage (1 – 15 mg) form as tablets or capsules for oral administration either alone or in combination with suitable adjuvants such as calcium carbonate, starch, lactose, talc, magnesium stearate and gum acacia.

Practical and presently preferred embodiments of the present invention are shown in the following Examples.

Modifications of the procedures shown in these Examples will be obvious to those skilled in the art, and these Examples do not limit the scope of the invention.

EXAMPLE 1

2'-Hydroxy-2-($\beta$-methylthioethyl)-5,9-dimethyl-6,7-benzomorphan

A mixture of 4.34 g of 2'-hydroxy-5,9-dimethyl-6,7-benzomorphan, 3.53 g of sodium bicarbonate, 2.44 g of $\beta$-chloroethyl methyl sulfide and 60 ml of dimethylformamide is refluxed for 4 hours. The precipitate produced is filtered off. The filtrate is concentrated under reduced pressure to remove the dimethylformamide. The residue is dissolved in 35 ml of 2N-HCl. The solution is washed with ether, basified with concentrated aqueous ammonia and extracted with chloroform. The extract is washed, dried and evaporated to dryness to give 2'-hydroxy-2-($\beta$-methylthioethyl)-5,9-dimethyl-6,7-benzomorphan. Recrystallization from ethanol-water yields a colorless product. M.P. 148° – 152.5°C.

IR $\nu_{paraffin}^{cm^{-1}}$ : 2600 (broad), 1611, 1580, 1495, 1242, 1070, 805, 795.

Anal. Calcd. for $C_{17}H_{25}NOS$: C, 70.06; H, 8.65; N, 4.81; S, 11.00%. Found: C, 70.20; H, 8.54; N, 4,73; S, 10.87%.

EXAMPLE 2

2'-Hydroxy-2-($\beta$-isopropylthioethyl)-5,9-dimethyl-6,7-benzomorphan

A mixture of 2.17 g of 2'-hydroxy-5,9-dimethyl-6,7-benzomorphan, 1.76 g of sodium bicarbonate, 2.01 g of $\beta$-bromoethyl isopropyl sulfide and 30 ml of dimethylformamide is refluxed for 4 hours. The precipitate produced is filtered off and the filtrate is evaporated to remove the solvent. The residual oil is dissolved in chloroform and the solution is washed with water. Concentration to dryness yields 2'-hydroxy-2-($\beta$-isopropylthioethyl)-5,9-dimethyl-6,7-benzomorphan. Recrystallization from ethyl acetate-petroleum ether gives a colorless product, M.P. 118° – 120°C.

IR $\nu_{paraffin}^{cm^{-1}}$ : 2600 (broad), 1620, 1580, 1490, 1240, 1140, 1100, 1070.

Anal. Calcd. for $C_{19}H_{29}NOS$: C, 71.42; H, 9.15; N, 4.38; S, 10.03%. Found: C, 71.82; H, 9.33; N, 4.22; S, 9.75%.

EXAMPLE 3

2'-Hydroxy-2-($\beta$-methylsulfonylethyl)-5,9-dimethyl-6,7-benzomorphan

A mixture of 2.2 g of 2'-hydroxy-5,9-dimethyl-6,7-benzomorphan, 1.7 g of sodium bicarbonate, 1.5 g of $\beta$-chloroethyl methyl sulfone and 30 ml of dimethylformamide is refluxed for 5 hours. The precipitate produced is removed by filtration and the filtrate is evaporated to leave 2'-hydroxy-2-($\beta$-methylsulfonylethyl)-5,9-dimethyl-6,7-benzomorphan as a crystalline solid. Recrystallization from 60% ethanol gives a colorless product, M.P. 177° – 178°C.

IR $\nu_{paraffin}^{cm^{-1}}$ : 2600 (broad), 1620, 1580, 1300, 1140, 820, 770.

Anal. Calcd. for $C_{17}H_{25}NO_3S$: C, 63.13; H, 7.79; N, 4.33; S, 9.91%. Found: C, 63.34; H, 7.68; N, 4.40; S, 9.62%.

EXAMPLE 4

2'-Hydroxy-2-($\beta$-methylthioethyl)-5,9-diethyl-6,7-benzomorphan

A mixture of 1.0 g of 2'-hydroxy-5,9-diethyl-6,7-benzomorphan, 0.51 g of sodium bicarbonate, 0.54 g of β-chloroethyl methyl sulfide and 30 ml of dimethylformamide is refluxed for 2 hours. The precipitate produced is filtered off and the filtrate is concentrated. The residue is dissolved in chloroform and the solution is washed with water, dried and evaporated to leave a crystalline product. Recrystallization from acetone gives 2'-hydroxy-2-(β-methylthioethyl)-5,9-diethyl-6,7-benzomorphan, M.P. 176° – 178°C.

IR $\nu_{paraffin}^{cm^{-1}}$ : 2650 (broad), 1615, 1580, 1490, 1240, 795.

Anal. Calcd. for $C_{19}H_{29}NOS$: C, 71.42; H, 9.15; N, 4.38; S, 10.04%. Found: C, 71.51; H, 9.15; N, 4.36; S, 9.75%.

EXAMPLE 5

2'-Hydroxy-2-(β-methylthioethyl)-5-ethyl-9-methyl-6,7-benzomorphan

A mixture of 1.0 g of 2'-hydroxy-5-ethyl-9-methyl-6,7-benzomorphan, 0.55 g of sodium bicarbonate, 0.55 g of β-chloroethyl methyl sulfide and 30 ml of dimethylformamide is refluxed for 2 hours. The precipitate produced is filtered off and the filtrate is concentrated. The residue is dissolved in chloroform and the solution is washed with water, dried and evaporated to leave a crystalline product. Recrystallization from acetone gives 2'-hydroxy-2-(β-methylthioethyl)-5-ethyl-9-methyl-6,7-benzomorphan, M.P. 166° – 172°C.

IR $\nu_{paraffin}^{cm^{-1}}$ : 2650 (broad), 1610, 1575, 1490, 1235, 790.

Anal. Calcd. for $C_{18}H_{27}NOS$: C, 70.77; H, 8.91; N, 4.59; S, 10.50%. Found: C, 71.07; H, 8.73; N, 4.66; S, 10.18%.

EXAMPLE 6

2'-Hydroxy-2-(β-methylthioethyl)-5-ethyl-6,7-benzomorphan

A mixture of 1.0 g of 2'-hydroxy-5-ethyl-6,7-benzomorphan, 0.58 g of sodium bicarbonate, 0.61 g of β-chloroethyl methyl sulfide and 30 ml of dimethylformamide is refluxed for 3 hours. The precipitate produced is removed by filtration and the filtrate is concentrated to dryness. The residual crystalline product is recrystallized from ethyl acetate to yield 2'-hydroxy-2-(β-methylthioethyl)-5-ethyl-6,7-benzomorphan, M.P. 187.5° – 192.5°C.

IR $\nu_{paraffin}^{cm^{-1}}$ : 2600 (broad), 1610, 1575, 1490, 1235, 800.

Anal. Calcd. for $C_{17}H_{25}NOS$: C, 70.06; H, 8.65, N, 4.81; S, 11.00%. Found: C, 70.12, H, 8.49; N. 4.90; S, 11.29%.

EXAMPLE 7

2'-Hydroxy-2-(β-methylthioethyl)-5-methyl-9-ethyl-6,7-benzomorphan

A mixture of 1.0 g of 2'-hydroxy-5-methyl-9-ethyl-6,7-benzomorphan, 0.55 g of sodium bicarbonate, 0.58 g of β-chloroethyl methyl sulfide and 30 ml of dimethylformamide is refluxed for 5 hours. The precipitate produced is filtered off and the filtrate is evaporated to remove the solvent. The residual crude product is recrystallized from acetone to give 2'-hydroxy-2-(β-methylthioethyl)-5-methyl-9-ethyl-6,7-benzomorphan, M.P. 155° – 159°C.

IR $\nu_{paraffin}^{cm^{-1}}$ : 2600 (broad), 1610, 1580, 1490, 920, 800.

Anal. Calcd. for $C_{18}H_{27}NOS$: C, 70.77; H, 8.91; N, 4.59; S, 10.50%. Found: C, 70.84; H, 8.89; N, 4.57; S, 10.23%.

EXAMPLE 8

2-(β-Methylthioethyl)-5-methyl-6,7-benzomorphan

A mixture of 0.90 g of 5-methyl-6,7-benzomorphan, 0.60 g of sodium bicarbonate, 0.58 g of β-chloroethyl methyl sulfide and 20 ml of ethanol is refluxed for 9 hours and concentrated to dryness. The residue is treated with ether and water. The ether layer is washed, dried and evaporated to leave an oily product, which is converted to the hydrochloride by treating with ether-hydrogen chloride. The crystalline solid obtained is recrystallized from methanol-acetone to give 2-(β-methylthioethyl)-5-methyl-6,7-benzomorphan hydrochloride, M.P. 252° – 255°C (dec.).

IR $\nu_{paraffin}^{cm^{-1}}$ : 2500 (broad), 1490, 760, 720.

Anal. Calcd. for $C_{16}H_{24}NClS$: C, 64.51; H, 8.12; N, 4.70; Cl, 11.90; S, 10.76%. Found: C, 64.87; H, 8.38; N, 4.71; Cl, 11.90; S, 10.42%.

EXAMPLE 9

2'-Hydroxy-2-(β-methylthioethyl)-5-phenyl-6,7-benzomorphan

A mixture of 1.0 g of 2'-hydroxy-5-phenyl-6,7-benzomorphan, 0.48 g of sodium bicarbonate, 0.46 g of β-chloroethyl methyl sulfide and 20 ml of dimethylformamide is stirred at 120°C for 14 hours and concentrated to dryness. The residue is treated with water to yield a crystalline product. Recrystallization from acetone gives 2'-hydroxy-2-(β-methylthioethyl)-5-phenyl-6,7-benzomorphan, M.P. 205° –208°C.

IR $\nu_{paraffin}^{cm^{-1}}$ : 2620 (broad), 1610, 1580, 810, 760, 700.

Anal. Calcd. for $C_{21}H_{25}NOS$: C, 74.29; H, 7.42; N, 4.13; S, 9.44%. Found: C, 74.26; H, 7.40; N, 4.07; S, 9.58%.

EXAMPLE 10

2'-Methoxy-2-(β-methylthioethyl)-5,9-dimethyl-6,7-benzomorphan

A mixture of 2.31 g of 2'-methoxy-5,9-dimethyl-6,7-benzomorphan, 1.20 g of sodium bicarbonate, 1.22 g of β-chloroethyl methyl sulfide and 30 ml of dimethylformamide is refluxed for 3 hours. The precipitate produced is filtered off and the filtrate is concentrated to remove the solvent. The residue is dissolved in ether and the solution is washed, dried and evaporated to leave 2'-methoxy-2-(β-methylthioethyl)-5,9-dimethyl-6,7-benzomorphan as viscous oil.

IR $\nu_{liq.}^{cm^{-1}}$ : 1610, 1585, 1490, 1240.

EXAMPLE 11

2'-Acetoxy-2-(β-methylthioethyl)-5,9-dimethyl-6,7-benzomorphan

A mixture of 2.9 g of 2'-hydroxy-2-(β-methylthioethyl)-5,9-dimethyl-6,7-benzomorphan, 10 ml of acetic anhydride and a few drops of pyridine is stirred at room temperature over night. The mixture is poured into ice-water, basified with aqueous potassium hydroxide and extracted with ether. The extract is washed, dried and evaporated to yield 2'-acetoxy-2-(β-methylthioethyl)-5,9-dimethyl-6,7-benzomorphan as viscous oil.

IR $\nu_{liq.}^{cm^{-1}}$ : 1760, 1610, 1585, 1495, 1210.

EXAMPLE 12

2-(β-Methylthioethyl)-6,7-benzomorphan

A mixture of 1.73 g of 6,7-benzomorphan, 1.20 g of sodium carbonate, 1.22 g of β-chloroethyl methyl sulfide and 30 ml of dimethylformamide is refluxed for 3 hours. The precipitate produced is filtered off and the filtrate is concentrated to remove the solvent. The residue is dissolved in ether and the solution is washed, dried and evaporated to yield 2-(β-methylthioethyl)-6,7-benzomorphan as viscous oil.

IR $\nu^{cm^{-1}}$: 1600 (weak), 1490, 1460, 760, 740.

EXAMPLE 13

2'-Hydroxy-2-(β-methylthioethyl)-4,5-dimethyl-6,7-benzomorphan

A mixture of 1.3 g of 2'-hydroxy-4,5-dimethyl-6,7-benzomorphan, 0.76 g of sodium bicarbonate, 0.86 g of β-chloroethyl methyl sulfide and 20 ml of dimethylformamide is refluxed for 3 hours. The precipitate produced is filtered off and the filtrate is concentrated under reduced pressure. The residual crude product is recrystallized from ethanol to yield 2'-hydroxy-2-(β-methylthioethyl)-4,5-dimethyl-6,7-benzomorphan, M.P. 188°–190°C.

IR $\nu^{cm^{-1}}$parraffin: 2600(broad), 1610, 1580, 1500, 1240, 875, 810.

Anal. Calcd. for $C_{17}H_{25}NOS$: C, 70.06; H, 8.65; N, 4.81; S, 11.00%.

Found: C, 69.86; H, 8.60; N, 4.71; S, 10.80%.

EXAMPLE 14

2'-Methoxy-2-(β-methylthioethyl)-5,9-diethyl-6,7-benzomorphan

A mixture of 2.8 g of 2'-methoxy-5,9-diethyl-6,7-benzomorphan, 1.3 g of sodium bicarbonate, 1.3 g of β-chloroethyl methyl sulfide and 30 milliliters of dimethylformamide is refluxed for 3 hours. The precipitate produced is filtered off and the filtrate is concentrated under reduced pressure. The residue is dissolved in chloroform and the solution is washed with water, dried and evaporated to yield 2'-methoxy-2-(β-methylthioethyl)-5,9-diethyl-6,7-benzomorphan as an oily product.

IR$\nu_{liq.}^{cm^{-1}}$: 1610, 1575, 1500, 1290, 1240, 1040, 850, 800.

This free base is treated with ether-hydrogen chloride to give a crystalline solid, which is recrystallized from acetonemethanol to yield 2'-methoxy-2-(β-methylthioethyl)-5,9-diethyl-6,7-benzomorphan hydrochloride, M.P. 239°–240°C. (dec.).

IR $\nu_{paraffin}^{cm^{-1}}$: 2450 (broad), 1610, 1575, 1495, 1290, 1240, 1040, 860.

It will be appreciated from the above examples that the relative proportions of reactants [II], i.e. the 6,7-berzomorphan derivative, and [III], i.e. the reactive derivative of an alcohol, may vary and generally the proportion of reactants II and III is in a molar ratio of 1:1 –2 and preferably 1:1.5.

Also, the amount of basic substance used is from about 0.5 to about 3 mol (preferably about 1 to about 2 mol) to 1 mol of reactant [II]; whereas the amount of solvent is from about 4 to 50 parts by weight, preferably about 8 to 30 parts by weight to 1 part by weight of reactant [II].

While the novel principles of the invention have been described, it will be understood that various omissions, modifications and changes in these principles may be made by one skilled in the art without departing from the spirit and scope of the invention.

What is claimed is:

1. An analgesic composition comprising an analgesically effective amount of the 6,7-benzomorphan derivative of the formula:

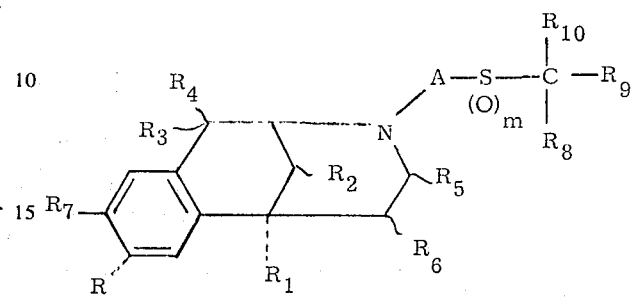

wherein R is a hydrogen atom, a hydroxyl group, a $C_1 - C_3$ alkoxy group or a $C_1 - C_8$ alkanoyloxy group; $R_1$ is a hydrogen atom, a $C_1- C_5$ alkyl group, a $C_2- C_{10}$ alkoxyalkyl group, a phenyl group a halophenyl group, an alkylphenyl group wherein the alkyl moiety has 1 to 3 carbon atoms or an alkoxyphenyl group wherein the alkoxy moiety has 1 to 3 carbon atoms; $R_3$ is a hydrogen atom or a hydroxyl group; $R_4$ is a hydrogen atom, a $C_1- C_3$ alkyl group, a phenyl group, a halophenyl group, an alkylphenyl group wherein the alkyl moiety has 1 to 3 carbon atoms or an alkoxyphenyl group wherein the alkoxy moiety has 1 to 3 carbon atoms, or $R_3$ and $R_4$ may form a $C_1 - C_3$ alkylidene group or a carbonyl group together with the carbon atom to which they are bonded; $R_2$, $R_5$, $R_6$, $R_7$, $R_8$, $R_{R9}$ and $R_{10}$ are each a hydrogen atom or a $C_1 - C_3$ alkyl group; A is a $C_1 - C_3$ alkylene group; and m is an integer of 0 to 2 or an acid addition salt thereof as the active ingredient and a pharmaceutically acceptble carrier or diluent.

2. The analgesic composition according to claim 1, wherein the active ingredient is the 6,7-benzomorphan derivative of the formula:

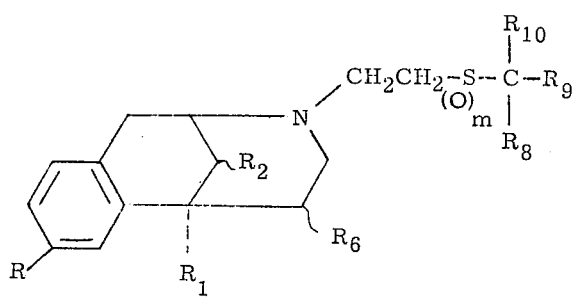

wherein R is a hydrogen atom, a hydroxyl group, a $C_1 - C_3$ alkoxy group or a $C_1 -C_8$ alkanoyloxy group; $R_1$ is a hydrogen atom, a $C_1 -C_5$ alkyl group or a phenyl group; $R_2$, $R_6$, $R_8$, $R_9$ and $R_{10}$ are each a hydrogen atom or $C_1-C_3$ alkyl group; and m is an integer of 0 to 2 or an acid addition salt.

3. The analgesic composition according to claim 1, wherein the active ingredient is the 6,7-benzomorphan derivative of the formula:

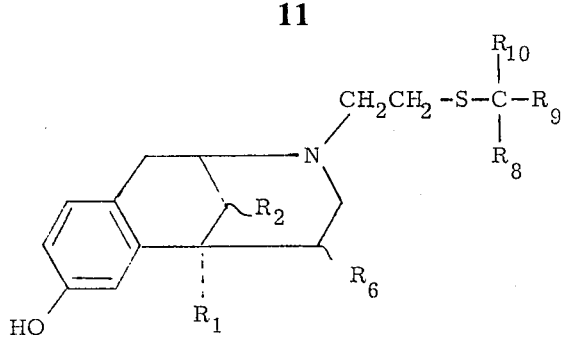

wherein $R_1$ is a hydrogen atom, a $C_1$–$C_3$ alkyl group or a phenyl group; $R_2$ and $R_6$ are each hydrogen atom or a $C_1$–$C_3$ alkyl group; and $R_8$, $R_9$ and $R_{10}$ are each a hydrogen atom or a methyl group or an acid addition salt.

4. The analgesic composition according to claim 1, wherein the active ingredient is 2'-hydroxy-2-($\beta$-methylthioethyl)-6,7-benzomorphan or an acid addition thereof.

5. The analgesic composition according to claim 1, wherein the active ingredient is 2'-hydroxy-2-($\beta$-methylthioethyl)-5,9-dimethyl-6,7-benzomorphan or an acid addition thereof.

6. The analgesic composition according to claim 1, wherein the active ingredient is 2'-hydroxy-2-($\beta$-methylthioethyl)-5-ethyl-6,7-benzomorphan or an acid addition thereof.

7. The analgesic composition according to claim 1, wherein the active ingredient is 2'-hydroxy-2-($\beta$-methylthioethyl)-5-ethyl-9-methyl-6,7-benzomorphan or an acid addition thereof.

8. The analgesic composition according to claim 1, wherein the active ingredient 2'-hydroxy-2-($\beta$-methylthioethyl)-5,9-diethyl-6,7-benzomorphan or an acid addition thereof.

9. The analgesic composition according to claim 1, wherein the active ingredient is 2'-methoxy-2-($\beta$-methylthioethyl)-5,9-dimethyl-6,7-benzomorphan or an acid addition thereof.

10. The analgesic composition according to claim 1, wherein the active ingredient is 2'-acetoxy-2-($\beta$-methylthioethyl)-5,9-dimethyl-6,7-benzomorphan or an acid addition thereof.

11. The analgesic composition according to claim 1, wherein the active ingredient is 2'-hydroxy-2-($\beta$-isopropylthioethyl)-5,9-dimethyl-6,7-benzomorphan or an acid addition thereof.

12. The analgesic composition according to claim 1, wherein the active ingredient is 2'-hydroxy-2-($\beta$-methylthioethyl)-5-methyl-6,7-benzomorphan or an acid addition thereof.

13. The analgesic composition according to claim 1, wherein the active ingredient is 2'-hydroxy-2-($\beta$-isopropylthioethyl)-5-ethyl-6,7-benzomorphan or an acid addition thereof.

14. The analgesic composition according to claim 1, wherein the active ingredient is 2'-hydroxy-2-($\beta$-methylthioethyl)-4,5-dimethyl-6,7-benzomorphan or an acid addition thereof.

15. The analgesic composition according to claim 1, wherein the effective amount of the 6,7-benzomorphan derivative or the acid addition salt thereof comprises a unit dosage of from 1–15 mg.

* * * * *